United States Patent [19]

LeMahieu

[11] Patent Number: 4,539,419
[45] Date of Patent: Sep. 3, 1985

[54] NAPHTHALENYLOXY SUBSTITUTED CARBOXYLIC ACIDS

[75] Inventor: Ronald A. LeMahieu, Caldwell, N.J.

[73] Assignee: Hoffmann-La Roche Inc., Nutley, N.J.

[21] Appl. No.: 490,823

[22] Filed: May 2, 1983

[51] Int. Cl.³ .............................................. C07C 69/76
[52] U.S. Cl. ................................... 560/053; 562/461; 562/466; 560/56; 568/328
[58] Field of Search .................... 560/53, 56; 562/461, 562/466; 514/532, 543, 569

[56] References Cited
FOREIGN PATENT DOCUMENTS
2118184  1/1983  United Kingdom ................. 560/53

Primary Examiner—Paul J. Killos
Attorney, Agent, or Firm—Jon S. Saxe; Bernard S. Leon; William G. Isgro

[57] ABSTRACT

Compounds of the formula

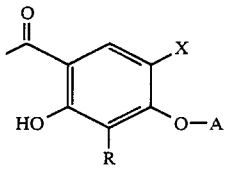

I wherein R is hydrogen or lower alkyl, X is hydrogen or halogen, and A is the group

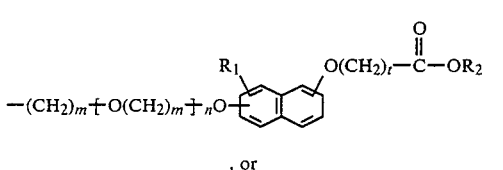

(a)

, or

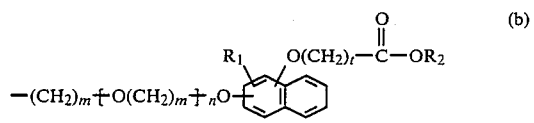

(b)

wherein $R_1$ is hydrogen, acyl or lower alkyl, $R_2$ is hydrogen or lower alkyl, m is an integer from 2 to 4, n is an integer from 1 to 3, and t is an integer from 1 to 5, provided that $R_1$ is adjacent to $-(CH_2)_m[O(CH_2)_m]_nO-$, and, when $R_2$ is hydrogen, salts thereof with pharmaceutically acceptable bases, are described. The compounds of formula I are useful as agents for the treatment of allergic conditions.

11 Claims, No Drawings

NAPHTHALENYLOXY SUBSTITUTED CARBOXYLIC ACIDS

BRIEF SUMMARY OF THE INVENTION

The invention relates to compounds of the formula

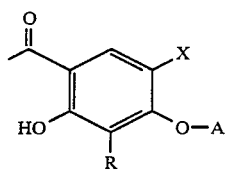

wherein R is hydrogen or lower alkyl, X is hydrogen or halogen, and A is

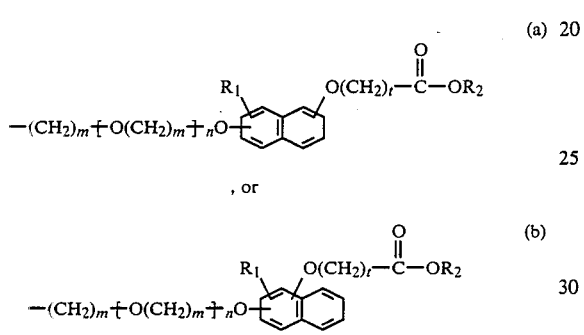

wherein $R_1$ is hydrogen, acyl or lower alkyl, $R_2$ is hydrogen or lower alkyl, m is an integer from 2 to 4, n is an integer from 1 to 3, and t is an integer from 1 to 5, provided that $R_1$ is adjacent to $-(CH_2)_{\overline{m}}[O(CH_2)_{m\overline{}}]_nO-$, and, when $R_2$ is hydrogen, salts thereof with pharmaceutically acceptable bases. The compounds of formula I are useful as agents for the treatment of allergic conditions.

In another aspect, the invention relates to intermediates of the formulas

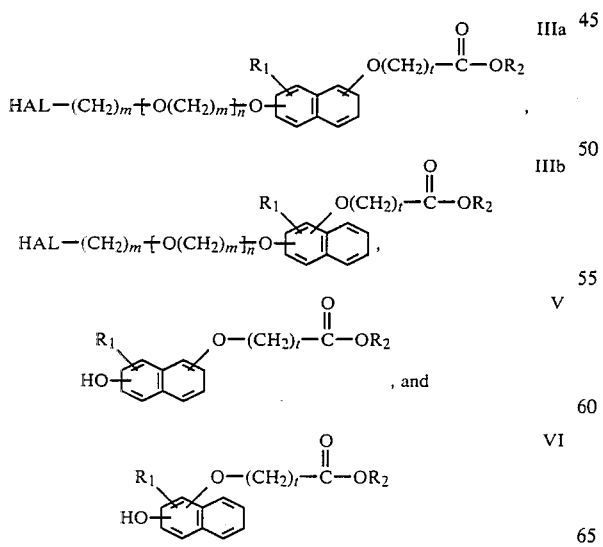

wherein HAL, $R_1$, $R_2$, m, n and t are previously described.

DETAILED DESCRIPTION OF THE INVENTION

As used herein, the term "lower alkyl" denotes a straight or branched chain saturated hydrocarbon containing 1 to 7 carbon atoms, for example, methyl, ethyl, propyl, isopropyl, butyl, t-butyl, neopentyl, pentyl, heptyl and the like. The term "halogen" denotes all the halogens, that is, bromine, chlorine, fluorine and iodine. The term "acyl" denotes an "alkanoyl" group derived from a aliphatic carboxylic acid of 1 to 7 carbon atoms, for example, formyl, acetyl, propionyl, and the like; and an "aroyl" group derived from an aromatic carboxylic acid, such as benzoyl and the like.

The invention relates to compounds of the formula

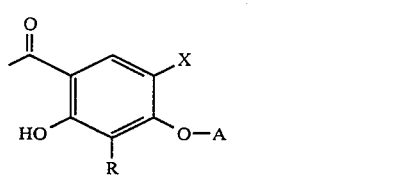

wherein R is hydrogen or lower alkyl, X is hydrogen or halogen, and A is the group

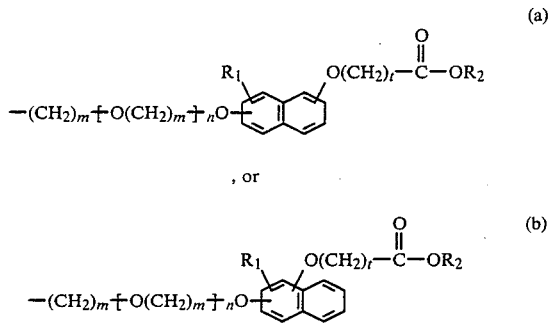

wherein $R_1$ is hydrogen, acyl or lower alkyl, $R_2$ is hydrogen or lower alkyl, n is an integer from 2 to 4, n is an integer from 1 to 3, and t is an integer from 1 to 5, provided that $R_1$ is adjacent to $-(CH_2)_{\overline{m}}[O(CH_2)_{m\overline{}}]_nO-$, and, when $R_2$ is hydrogen, salts thereof with pharmaceutically acceptable bases.

A preferred group of compounds of formula I are those in which A is

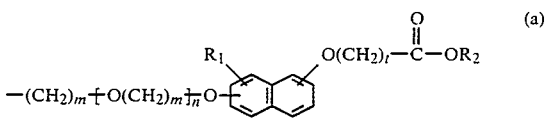

and X is hydrogen, R is lower alkyl, $R_1$ is alkanoyl, and $R_2$ is hydrogen.

A more preferred group of compounds of formula I are those in which A is as immediately above, and X is hydrogen, R is propyl, $R_1$ is acetyl, $R_2$ is hydrogen, m is 2 or 3, and t is 1 or 3.

A most preferred group of compounds of formula I are those in which A is

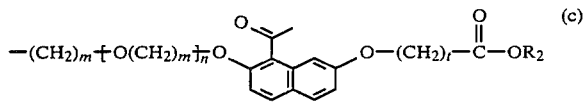

and X is hydrogen, R is propyl, $R_2$ is hydrogen, m is 2 or 3, and t is 1 or 3.

Preferred compounds of formula I are:

[[8-Acetyl-7-[3-[3-(4-acetyl-3-hydroxy-2-propylphenoxy)propoxy]propoxy]-2-naphthalenyl]oxy]acetic acid;

[[8-Acetyl-7-[2-[2-(4-acetyl-3-hydroxy-2-propylphenoxy)ethoxy]ethoxy]-2-naphthalenyl]oxy]acetic acid;

[[8-Acetyl-7-[2-[2-[2-(4-acetyl-3-hydroxy-2-propylphenoxy)ethoxy]ethoxy]ethoxy]-2-naphthalenyl]oxy]acetic acid;

[[8-Acetyl-7-[2-[2-[2-[2-(4-acetyl-3-hydroxy-2-propyphenoxy]ethoxy]ethoxy]ethoxy]-2-naphthalenyl]oxy]acetic acid; and 4-[[8-Acetyl-7-[2-[2-(4-acetyl-3-hydroxy-2-propylphenoxy)ethoxy]ethoxy]-2-naphthalenyl]oxy]butanoic acid.

Exemplary of compounds of formula I are:

3-[[8-Acetyl-7-[3-[3-(4-acetyl-3-hydroxy-2-propylphenoxy)propoxy]propoxy]-2-naphthalenyl]oxy]propanoic acid;

4-[[8-Acetyl-7-[3-[3-(4-acetyl-3-hydroxy-2-propylphenoxy)propoxy]propoxy]-2-naphthalenyl]oxy]butanoic acid;

6-[[8-Acetyl-7-[3-[3-(4-acetyl-3-hydroxy-2-propylphenoxy)propoxy]propoxy]-2-naphthalenyl]oxy]hexanoic acid;

3-[[8-Acetyl-7-[2-[2-(4-acetyl-3-hydroxy-2-propylphenoxy)ethoxy]ethoxy]-2-naphthalenyl]oxy]propanoic acid;

5-[[8-Acetyl-7-[2-[2-(4-acetyl-3-hydroxy-2-propylphenoxy)ethoxy]ethoxy]-2-naphthalenyl]oxy]pentanoic acid;

3-[[8-Acetyl-7-[2-[2-[2-(4-acetyl-3-hydroxy-2-propylphenoxy)ethoxy]ethoxy]ethoxy]-2-naphthalenyl]oxy]propanoic acid;

4-[[8-Acetyl-7-[2-[2-[2-(4-acetyl-3-hydroxy-2-propylphenoxy)ethoxy]ethoxy]ethoxy]-2-naphthalenyl]oxy]butanoic acid;

3-[[8-Acetyl-7-[2-[2-[2-[2-(4-acetyl-3-hydroxy-2-propylphenoxy)ethoxy]ethoxy]ethoxy]ethoxy]-2-naphthalenyl]oxy]propanoic acid;

4-[[8-Acetyl-7-[2-[2-[2-[2-(4-acetyl-3-hydroxy-2-propylphenoxy)ethoxy]ethoxy]ethoxy]ethoxy]-2-naphthalenyl]oxy]butanoic acid;

[[7-[2-[2-(4-Acetyl-3-hydroxy-2-propylphenoxy)ethoxy]ethoxy]-2-naphthalenyl]oxy]acetic acid;

[[7-[2-[2-[2-(4-Acetyl-3-hydroxy-2-propylphenoxy)ethoxy]ethoxy]ethoxy]-2-naphthalenyl]oxy]acetic acid;

[[7-[2-[2-[2-[2-(4-Acetyl-3-hydroxy-2-propylphenoxy)ethoxy]ethoxy]ethoxy]ethoxy]-2-naphthalenyl]oxy]acetic acid;

[[4-[2-[2-(4-Acetyl-3-hydroxy-2-propylphenoxy)ethoxy]ethoxy]-2-naphthalenyl]oxy]acetic acid;

[[4-[2-[2-[2-(4-Acetyl-3-hydroxy-2-propylphenoxy)ethoxy]ethoxy]ethoxy]-2-naphthalenyl]oxy]acetic acid;

[[5-[2-[2-(4-Acetyl-3-hydroxy-2-propylphenoxy)ethoxy]ethoxy]-1-naphthalenyl]oxy]acetic acid;

[[5-[2-[2-[2-(4-Acetyl-3-hydroxy-2-propylphenoxy)ethoxy]ethoxy]ethoxy]-1-naphthalenyl]oxy]acetic acid;

[[5-[2-[2-[2-[2-(4-Acetyl-3-hydroxy-2-propylphenoxy)ethoxy]ethoxy]ethoxy]ethoxy]-1-naphthalenyl]oxy]acetic acid;

[[4-[2-[2-(4-Acetyl-3-hydroxy-2-propylphenoxy)ethoxy]ethoxy]-1-naphthalenyl]oxy]acetic acid;

[[4-[2-[2-[2-(4-Acetyl-3-hydroxy-2-propylphenoxy)ethoxy]ethoxy]ethoxy]-1-naphthalenyl]oxy]acetic acid;

[[3-Acetyl-4-[2-[2-(4-acetyl-3-hydroxy-2-propylphenoxy)ethoxy]ethoxy]-1-naphthalenyl]oxy]acetic acid;

[[3-Acetyl-4-[2-[2-[2-(4-acetyl-3-hydroxy-2-propylphenoxy)ethoxy]ethoxy]ethoxy]-1-naphthalenyl]oxy]acetic acid;

[[6-Acetyl-5-[2-[2-(4-acetyl-3-hydroxy-2-propylphenoxy)ethoxy]ethoxy]-1-naphthalenyl]oxy]acetic acid;

[[6-Acetyl-5-[2-[2-[2-[2-(4-acetyl-3-hydroxy-2-propylphenoxy)ethoxy]ethoxy]ethoxy]ethoxy]-1-naphthalenyl]oxy]acetic acid;

[[6-Acetyl-5-[2-[2-(4-acetyl-3-hydroxy-2-propylphenoxy)ethoxy]ethoxy]-2-naphthalenyl]oxy]acetic acid;

[[6-Acetyl-5-[2-[2-[2-(4-acetyl-3-hydroxy-2-propylphenoxy)ethoxy]ethoxy]ethoxy]-2-naphthalenyl]oxy]acetic acid;

[[7-acetyl-8-[3-[3-(4-acetyl-3-hydroxy-2-propylphenoxy)propoxy]propoxy]-2-naphthalenyl]oxy]acetic acid;

[[7-acetyl-8-[2-[2-(4-acetyl-3-hydroxy-2-propylphenoxy)propoxy]propoxy]-2-naphthalenyl]oxy]acetic acid; and the like.

In accordance with the invention, the compounds of formula I can be prepared as set forth in Reaction Schemes I and II.

Reaction Scheme I

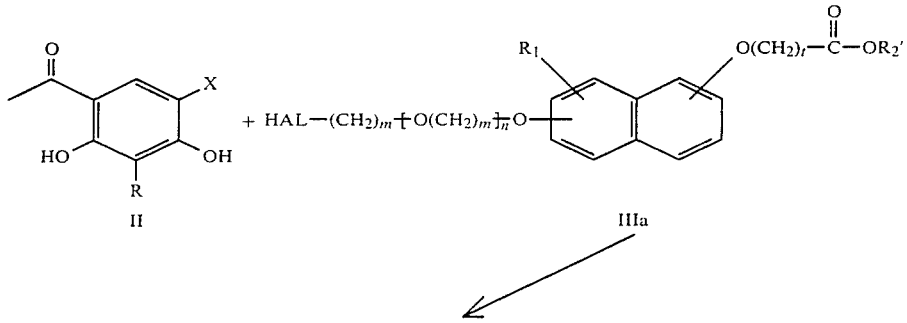

-continued
Reaction Scheme I

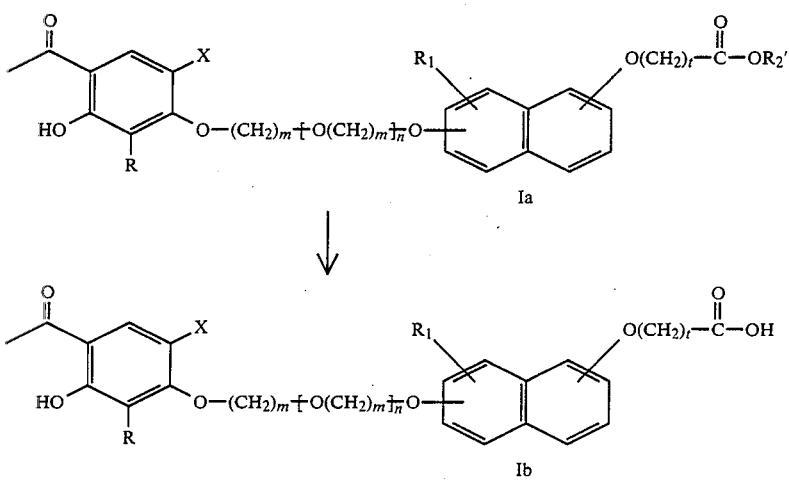

wherein R, R₁, m, n, t and X are as previously described, and R₂' is lower alkyl and HAL is halogen.

In Reaction Scheme I, the reaction of a compound of formula II, which are known compounds or can be prepared according to known procedures, with a compound of formula IIIa to yield a compound of formula Ia is carried out under anhydrous conditions in an inert solvent, for example, acetone, methylethyl ketone, diethyl ketone, dimethylformamide or the like, at the reflux temperature of the reaction mixture, in dimethylformamide, preferably at a temperature in the range of 70°-100° C., and in the presence of an acid acceptor, for example, potassium carbonate or the like. The preferred solvent is a mixture of acetone and dimethylformamide. The resulting compound of formula Ia can be recovered utilizing conventional methods, for example, crystallization, chromatography or the like.

A resulting compound of formula Ia can be converted to a compound of formula Ib by hydrolysis which is carried out with an alkali metal hydroxide, for example, sodium hydroxide, potassium hydroxide or the like, in a mixture of water and a water miscible alcohol, for example, methanol, ethanol or the like, at a temperature in the range of from about room temperature to the reflux temperature. The resulting compound of formula Ib can be recovered utilizing conventional methods, for example, crystallization, chromatography or the like.

Reaction Scheme II

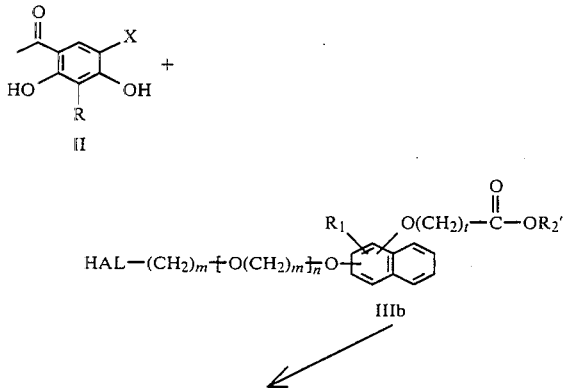

-continued
Reaction Scheme II

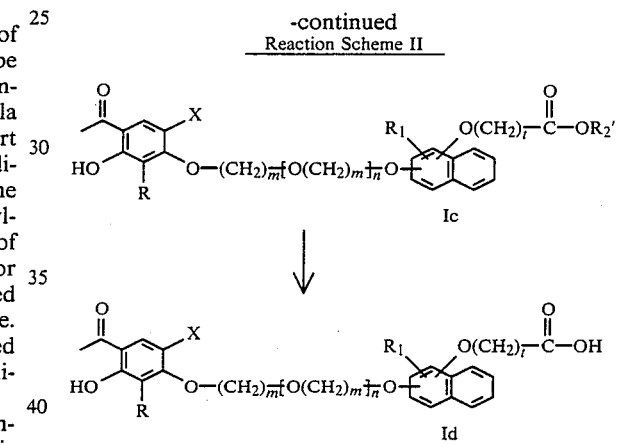

wherein R, R₁, R₂', m, n, t, X and HAL are as previously described.

In Reaction Scheme II, the reaction of a compound of formula II with a compound of formula IIIb to yield a compound of formula Ic is carried out under anhydrous conditions in an inert solvent, for example, acetone, methylethyl ketone, diethyl ketone, dimethylformamide or the like, at the reflux temperature of the reaction mixture, in dimethylformamide, preferably at a temperature in the range of 70°-100° C., and in the presence of an acid acceptor, for example, potassium carbonate or the like. The preferred solvent is a mixture of acetone and dimethylformamide. The resulting compound of formula Ic can be recovered utilizing conventional methods, for example, crystallization, chromatography or the like.

A resulting compound of formula Ic can be converted to a compound of formula Id by hydrolysis which is carried out with an alkali metal hydroxide, for example, sodium hydroxide, potassium hydroxide or the like, in a mixture of water and a water miscible alcohol, for example, methanol, ethanol or the like, at a temperature in the range of from about room temperature to the reflux temperature. The resulting compound of formula Id can be recovered utilizing conventional methods, for example, crystallization, chromatography or the like.

The starting materials for the preparation of the compounds of formula I can be prepared according to Reaction Schemes III, IV, V and VI which follow:

Reaction Scheme III

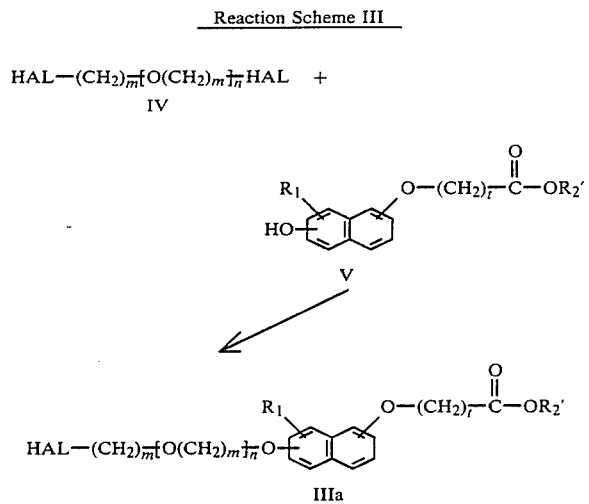

wherein $R_1$, $R_2'$, m, n, t and HAL are as previously described.

In Reaction Scheme III, the reaction of a compound of formula IV, which compounds are known or can be prepared by known procedures, with a compound of formula V to yield a compound of formula IIIa can be carried out under anhydrous conditions in an inert solvent, for example, acetone, methylethyl ketone, diethyl ketone, dimethylformamide or the like, at the reflux temperature of the reaction mixture, in dimethylformamide, preferably at a temperature in the range of 70°–100° C., and in the presence of an acid acceptor, for example, potassium carbonate or the like. The preferred solvent is a mixture of acetone and dimethylformamide. The resulting compound of formula IIIa can be recovered utilizing conventional methods, for example, crystallization, chromatography or the like.

A preferred set of reaction conditions involves the use of sodium hydride as the base in an anhydrous, inert solvent such as dimethylformamide at a temperature in the range of 25°–70°.

Reaction Scheme IV

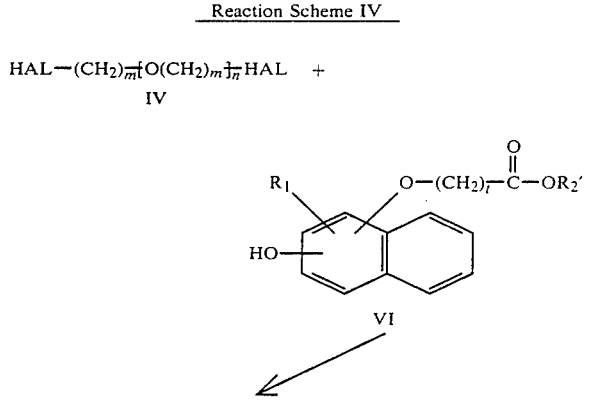

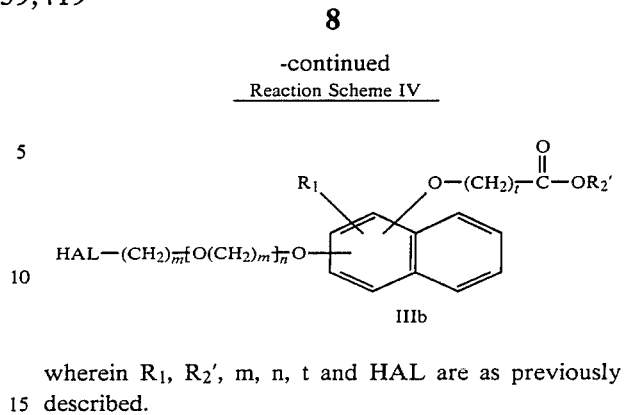

wherein $R_1$, $R_2'$, m, n, t and HAL are as previously described.

In Reaction Scheme IV, the reaction of a compound of formula IV, which compounds are known or can be prepared by known procedures, with a compound of formula VI to yield a compound of formula IIIb can be carried out under anhydrous conditions in an inert solvent, for example, acetone, methylethyl ketone, diethyl ketone, dimethylformamide or the like, at the reflux temperature of the reaction mixture, in dimethylformamide, preferably at a temperature in the range of 70°–100° C., and in the presence of an acid acceptor, for example, potassium carbonate or the like. The preferred solvent is a mixture of acetone and dimethylformamide. The resulting compound of formula IIIb can be recovered utilizing conventional methods, for example, crystallization, chromatography or the like.

A preferred set of reaction conditions involves the use of sodium hydride as the base in an anhydrous, inert solvent such as dimethylformamide at a temperature in the range of 25°–70°.

Reaction Scheme V

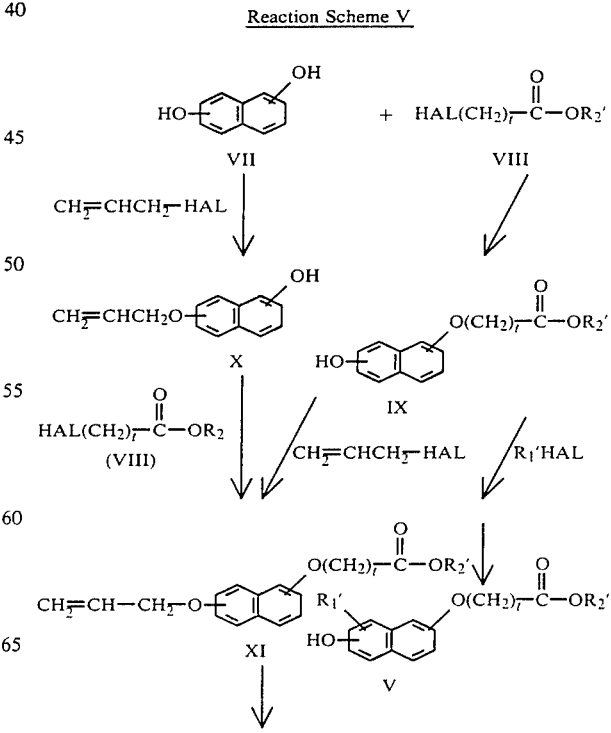

-continued
Reaction Scheme V

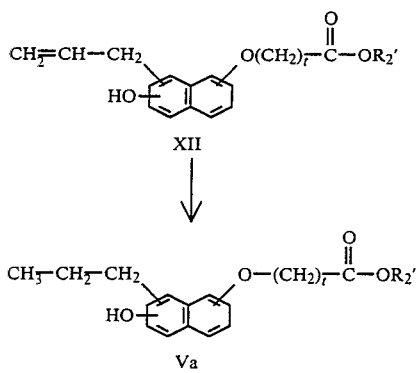

wherein R₂' and t are as previously described, and R₁' is acyl.

In Reaction Scheme V, the reaction of a compound of formula VII, which are known compounds or can be prepared according to known procedures, with a compound of formula VII, which are known compounds or can be prepared according to known procedures, to yield a compound of formula IX is carried out under anhydrous conditions in an inert solvent, for example, acetone, methylethyl ketone, diethyl ketone, dimethylformamide or the like, preferably at a temperature in the range of 25°–70° C., and in the presence or an acid acceptor, for example, potassium carbonate or the like. The resulting compound of formula IX can be recovered utilizing conventional methods, for example, crystallization, chromatography or the like.

A resulting compound of formula IX can be converted to a compound of formula V by reaction with an alkanoyl halide such as acetyl chloride and an aluminum halide such as aluminum chloride in an inert solvent such as dichloroethane nitromethane or the like at a temperature in the range of 25°–70° C. The resulting compound of formula V can be recovered using conventional methods, for example, crystallization, chromatography or the like. Alternatively a compound of formula IX can be converted to a compound of formula XI by reaction with an allyl halide, such as allyl bromide, and an alkali metal carbonate, such as potassium carbonate in an inert solvent, for example, acetone or methylethyl ketone, at a temperature in the range of 25°–70° C. The resulting product of formula XI can be recovered using conventional methods.

A compound of formula XI can also be prepared by reaction of a compound of formula VII with an allyl halide and an alkali metal carbonate in acetone. The resulting product of formula X can be recovered by conventional methods. A compound of formula X can be converted to a compound of formula XI by reaction with compound VIII in an inert solvent such as acetone and using a base such as potassium carbonate at the reflux temperature of the solvent. The resulting compound of formula XI can be recovered by conventional means.

A compound of formula XI can be rearranged to a compound of formula XII by heating at a temperature of the range of 170°–200° C., either without solvent or using a solvent such as diethylaniline. The resulting product of formula XII can be recovered using conventional methods.

A compound of formula XII can be converted to a compound of formula Va by shaking in an inert solvent such as ethyl acetate in a hydrogen atmosphere in the presence of a catalyst such as palladium on carbon. The resulting compound of formula Va can be recovered by conventional means.

Reaction Scheme VI

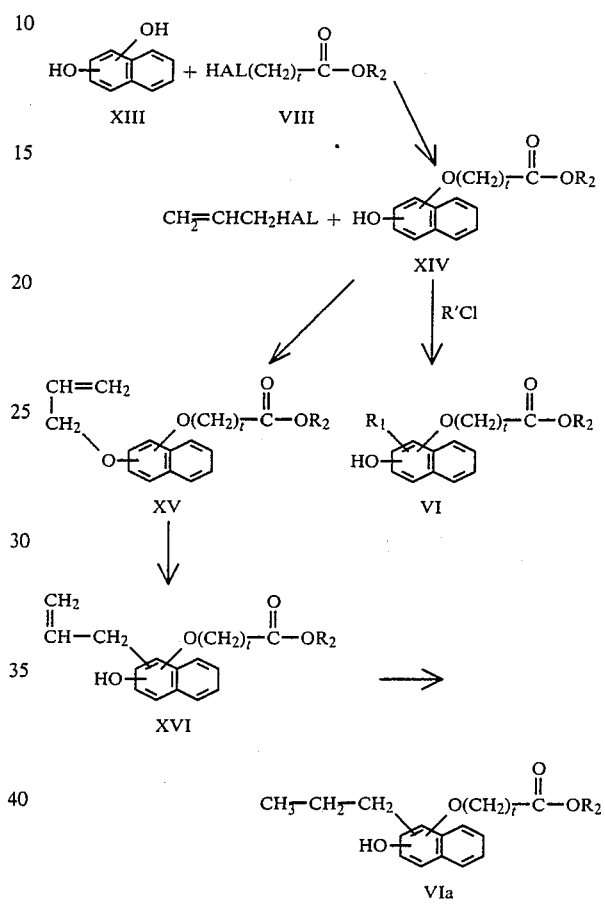

In Reaction Scheme VI, the reaction of a compound of formula XIII, which are a known compounds, with a compound of formula VIII is carried out under anhydrous conditions in an inert solvent such as acetone or methylethyl ketone, at a temperature in the range of 25°–70° C., in the presence of a base such as potassium carbonate or the like. The resulting compound of formula XIV can be recovered using conventional methods.

A compound of formula XIV can be converted to a compound of formula VI by reaction with an alkanoyl halide, such as acetyl chloride and an aluminum halide, such as aluminum chloride, in an inert solvent such as dichloroethane or nitromethane, at a temperature in the range of 25°–70° C. The product of formula VI can be recovered by conventional means. Alternatively, a compound of formula XIV can be converted to a compound of formula XV by reaction with an allyl halide, such as allyl bromide, and an alkali metal carbonate, such as potassium carbonate, in an inert solvent, for example, acetone, at a temperature in the range of 25°–70° C. The resulting compound of formula XV can be recovered using conventional methods.

A compound of formula XV can be rearranged to a compound of formula XVI by heating at a temperature in the range of 170°–200° C. either without solvent or using a solvent such as diethylaniline. The resulting product of formula XVI can be recovered by conventional means. A compound of formula XVI can be converted to a compound of formula VIa by shaking in an inert solvent such as ethyl acetate, in a hydrogen atmosphere in the presence of a catalyst such as palladium on carbon. The resulting compound of formula VIa can be recovered by conventional means.

Alternatively, the intermediates of formula V can be prepared by reacting a dihydroxynaphthalene of formula VII, which are known compounds or can be prepared according to known procedures, with an acyl halide under Friedel-Crafts conditions to provide an ortho-acyldihydroxynaphthalene. The ortho-acyldihydroxynaphthalene can then be reacted with a halo ester of formula VIII to give a compound of formula V wherein $R_1$ is acyl. Compounds of formula V wherein $R_1$ is lower alkyl are known compounds or can be prepared according to known procedures.

Intermediates of formula VI can be prepared by reacting a dihydroxynaphthalene of formula XIII, which are known compounds or can be prepared according to known procedures, with an acyl halide under Friedel-Crafts conditions to provide an acyl dihydroxynaphthalene. This acyl dihydroxynaphthalene can then be reacted with a halo esters of formula VIII to give a compound of formula VI wherein $R_1$ is acyl. Compounds of formula VI wherein $R_1$ is lower alkyl are known compounds or can be prepared according to known procedures.

This invention also relates to the pharmaceutically acceptable salts of the naphthalenyloxy carboxylic acid derivatives of formula I, wherein $R_2$ is hydrogen. Said salts can be prepared by reacting an acid of formula I with a base having a non-toxic, pharmacologically and pharmaceutically acceptable cation. In general, any base which will form a salt with a carboxylic acid and whose pharmacological properties will not cause an adverse physiological effect when ingested by a warmed blooded anmial is considered as being within the scope of this invention. Suitable bases thus include, for example, the alkali metal and alkaline earth metal hydroxides, carbonates, for example, sodium hydroxide, potassium hydroxide, calcium hydroxide, potassium carbonate and the like, ammonia, primary, secondary and tertiary amines, such as monoalkylamines, dialkylamines, trialkylamines, nitrogen containing heterocyclic amines, for example, piperidine, amino acids such as lysine, and the like. The pharmaceutically acceptable salts thus produced are the functional equivalent of the corresponding naphthalenyloxycarboxylic acids of formula I and one skilled in the art will appreciate that, to the extent that the salts of the invention are useful in therapy, the variety of salts encompassed by this invention are limited only by the criterion that the bases employed in forming the salts be both non-toxic and physiologically acceptable.

The compounds of formula I of the invention and their pharmaceutically acceptable salts are useful in the treatment of disorders in which slow reacting substance of anaphylaxis (SRS-A) is a mediator. The compounds of formula I and their pharmaceutically acceptable salts are therefore useful in the treatment of allergic disorders which include skin afflictions, hay fever, chronic bronchitis, obstructive airways diseases such as asthma, allergic conditions of the eye, and allergic conditions of the gastro-intestinal tract, such as food allergies.

The useful antiallergic activity of the compounds of formula I and their pharmaceutically acceptable salts is demonstrated in vitro and in warm-blooded animals utilizing standard procedures. Exemplary of such procedures are:

(a) Guinea Pig Ileum, In Vitro:

The guinea pig ileum bioassay system has been described by Orange and Austen, Adv. Immunol. 10: 105–144 (1969). A 1.5 cm segment is removed from animals weighing 300–400 g and suspended in an organ bath containing 10 ml of Tyrodes solution with $10^{-6}$M atropine sulfate and $10^{-6}$M pyrilamine maleate. The bath is maintained at 37° C. and aerated with a mixture of 95% oxygen and 5% carbon dioxide. The SRS-A utilized in this screen is obtained by challenging chopped lung fragments from actively sensitized guinea pigs with egg albumin, in vitro. A dose-response curve to SRS-A challenge is established for the ileum. The dose of SRS-A which gives 50% of the maximal contraction ($EC_{50}$) is then used for subsequent challenge. The drug concentration which inhibits, by 50%, the SRS-A-induced constriction of the guinea pig ileum is determined. In this bioassay system the standard SRS-A antagonist, 7-[3-(4-acetyl-3-hydroxy-2-propylphenoxy)-2-hydroxypropoxy]-4-oxo-8-propyl-4H-1-benzopyran-2-carboxylic acid, has an $IC_{50}$ of $3.5 \times 10^{-8}$M.

TABLE I

| Test Compound | Guinea Pig Ileum In Vitro $IC_{50}(M)$ |
| --- | --- |
| [[8-acetyl-7-[3-[3-(4-acetyl-3-hydroxy-2-propylphenoxy)propoxy]propoxy]-2-naphthalenyl]oxy] acetic acid | $1.5 \times 10^{-7}$ |
| [[8-acetyl-7-[2-[2-(4-acetyl-3-hydroxy-2-propylphenoxy)ethoxy]ethoxy]-2-naphthalenyl]oxy] acetic acid | $1 \times 10^{-6}$ |
| [[8-acetyl-7-[2-[2-[2-(4-acetyl-3-hydroxy-2-propylphenoxy)ethoxy]ethoxy]ethoxy]-2-naphthalenyl]oxy] acetic acid | $3 \times 10^{-7}$ |
| [[8-acetyl-7-[2-[2-[2-[2-(4-acetyl-3-hydroxy-2-propylphenoxy)ethoxy]ethoxy]ethoxy]ethoxy]-2-naphthalenyl]oxy] acetic acid | $1 \times 10^{-7}$ |
| 4-[[8-acetyl-7-[2-[2-(4-acetyl-3-hydroxy-2-propylphenoxy)ethoxy]ethoxy]-2-naphthalenyl]oxy]butanoic acid | $7 \times 10^{-7}$ |

A compound of formula I or a salt thereof when $R_2$ is hydrogen, or a composition containing a therapeutically effective amount of a compound of formula I or a salt thereof, when $R_2$ is hydrogen, can be administered by methods well known in the art. Thus, a compound of formula I, or a salt thereof when $R_2$ is hydrogen, can be administered either singly or with other pharmaceutical agents, for example, antihistamines, mediator release inhibitors, methyl xanthines, $B_2$ agonists or antiasthmatic steroids which as prednisone and prednisolone, orally, parenterally, rectally or by inhalation, for example, in the form of an aerosol, micropulverized powder or nebulized solution. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for exsmple, in admixture with sugar or other sweetening agents, flavoring agents, colorants, thickeners and other conventional pharmaceutical excipients. For parenteral administration, they can be administered in solutions or suspension, for example, as an aqueous or peanut oil solution or suspension using excipients and carriers conventional for this mode of administration. For administration as aerosols, they can be dissolved in a suitable pharmaceutically acceptable solvent, for example, ethyl alcohol or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, that is one which on activation releases a predetermined effective dose of the aerosol composition.

In the practice of the invention, the dose of a compound of formula I or a salt thereof when $R_2$ is hydrogen to be administered and the frequency of administration will be dependent on the potency and duration of activity of the particular compound of formula I or salt to be administered and on the route of administration, as well as the severity of the condition, age of the mammal to be treated and the like. Doses of a compound of formula I or a salt thereof when $R_2$ is hydrogen contemplated for use in practicing the invention are in the range of from about 25 to about 1000 mg per day, preferably about 25 to about 250 mg either as a single dose or in divided doses per day.

The Examples which follow further illustrate the invention. All temperatures are in degrees centigrade, unless otherwise stated.

EXAMPLE 1

Preparation Of [(7-Hydroxy-2-Naphthalenyl)Oxy]Acetic Acid Methyl Ester

A mixture of 32 g of 2,7-dihydroxynaphthalene and 36 g of anhydrous potassium carbonate in 250 ml of anhydrous acetone was stirred at 22° for 2 hours and 40 minutes. Methyl bromoacetate (20.8 ml) was added and stirring at room temperature was continued for 19 hours. The reaction mixture was filtered and the solid was washed well with acetone. The filtrate was concentrated in vacuo and the residue was acidified and extracted with methylene chloride. The methylene chloride extract was washed with 1N sodium hydroxide (3×200 ml). The combined aqueous extract was left at room temperature for 16 hours and then acidified and extracted with ethyl acetate. The extract was washed with saturated sodium bicarbonate solution. The insoluble sodium salt which formed was filtered, combined with the aqueous layer and acidified. The product was extracted with ethyl acetate and the dried (magnesium sulfate) extract was concentrated in vacuo to a solid (17 g). This was esterified by refluxing in 300 ml of methanol containing 4 ml of concentrated sulfuric acid for 5.5 hours. The solvent was removed in vacuo and the residue was taken up in methylene chloride and washed with sodium bicarbonate solution. The methylene chloride was removed in vacuo and the residue was crystallized from methylene chloride-hexane to give 12.8 g, mp 122°–123°, of [(7-hydroxy-2-naphthalenyl)oxy]acetic acid methyl ester. An additional 2.3 g was obtained by chromatography of the filtrate on 200 g of silica gel using 10% ethyl acetate toluene. The total yield was 33%.

EXAMPLE 2

Preparation of [(8-acetyl-7-hydroxy-2-naphthalenyl)oxy]acetic acid methyl ester

To a mixture of 5.8 g of aluminum chloride in 100 ml of dichloroethane was added 3.1 ml of acetyl chloride followed by 8.0938 g of [(7-hydroxy-2-naphthalenyl)oxy]acetic acid methyl ester. The mixture was stirred at room temperature for 2 hours and then at reflux for 19 hours. The reaction mixture was cooled, 100 ml of 6 N hydrochloric acid was added and, after shaking well, the product was extracted with methylene chloride. The extract was washed with sodium bicarbonate solution, dried (magnesium sulfate) and concentrated in vacuo to a solid which was recrystallized from methylene chloride-ether to give 6.030 g (63% yield), mp 113°–114°, of [(8-acetyl-7-hydroxy-2-naphthalenyl)oxy]acetic acid methyl ester. An additional 0.878 g of product was obtained on concentration of the filtrate to a smaller volume.

EXAMPLE 3

Preparation of [[8-acetyl-7-[3-(3-bromopropoxy)propoxy]-2-naphthalenyl]oxy]acetic acid methyl ester Under an argon atmosphere, 1 g of [8-acetyl-7-hydroxy-2-naphthalenyl)oxy]acetic acid methyl ester was added to a suspension of 0.16 g of 60% sodium hydride in 15 ml of anhydrous dimethylformamide. The mixture was stirred at room temperature for 40 minutes and then 4.75 g of bis(3-bromopropyl)ether was added. The mixture was stirred at room temperature for 20 hours. The mixture was concentrated in vacuo to an oil which was dissolved in ethyl acetate, washed with water and concentrated to give an oil which was purified by column chromatography using 7.5% ethyl acetate-toluene to yield 1 g (60%) of [[8-acetyl-7-[3-(3-bromopropoxy)propoxy]-2-naphthalenyl]oxy] acetic acid methyl ester as an oil.

EXAMPLE 4

Preparation of [[8-acetyl-7-[3-[3-(4-acetyl-3-hydroxy-2-propylphenoxy)propoxy]propoxy]-2-naphthalenyl]oxy]acetic acid methyl ester A mixture of 1.73 g of [[8-acetyl-7-[3-(3-bromopropoxy)propoxy]-2-naphthalenyl]oxy]acetic acid methyl ester, 0.89 g of 1-(2,4-dihydroxy-3-propylphenyl)ethanone and 0.79 g of anhydrous potassium carbonate in 33 ml of anhydrous acetone and 11 ml of anhydrous dimethylformamide was stirred at reflux for 18 hours. The mixture was filtered and filtrate was concentrated in vacuo to an oil. Purification by high pressure liquid chromatography (10% ethyl acetate-toluene) gave 1.2 g (56%) of [[8-acetyl-7-[3-[3-(4-acetyl-3-hydroxy-2-propylphenoxy)propoxy]propoxy]-2-naphthalenyl]oxy]acetic acid methyl ester.

EXAMPLE 5

Preparation of
[[8-acetyl-7-[3-[3-(4-acetyl-3-hydroxy-2-propylphenoxy)propoxy]propoxy]-2-naphthalenyl]oxy]acetic acid A mixture of 1.2 g of [[8-acetyl-7-[3-[3-(4-acetyl-3-hydroxy-2-propylphenoxy)propoxy]propoxy]-2-naphthalenyl]oxy]acetic acid methyl ester and 21 ml of 1N sodium hydroxide in 42 ml of methanol was stirred at reflux for 1 hour. The methanol was removed in vacuo and the aqueous solution was washed with ethyl acetate. The aqueous layer was acidified with 3N hydrochloric acid to pH 3 and the oil was extracted with chloroform. The extract was dried (magnesium sulfate) and concentrated to give an oil which was triturated with ether-cyclohexane and filtered to yield 0.85 g, mp 101°–104° C. (73%) of [[8-acetyl-7-[3-[3-(4-acetyl-3-hydroxy-2-propylphenoxy)propoxy]propoxy]-2-naphthalenyl]oxy]acetic acid.

EXAMPLE 6

Preparation of
[[8-acetyl-7-[2-(2-bromoethoxy)ethoxy]-2-naphthalenyl]oxy]acetic acid methyl ester Under an argon atmosphere, 2 g of [[8-acetyl-7-hydroxy-2-naphthalenyl]oxy]acetic acid methyl ester was added to a suspension of 0.32 g of 60% sodium hydride in 30 ml of anhydrous dimethylformamide. The mixture was stirred at room temperature for 30 minutes and then 8.5 g of bis-(2-bromoethyl)ether was added and the mixture was stirred at room temperature for 20 hours. The solvent was removed and residual oil was purified by high pressure liquid chromatography using 7% ethyl acetate-toluene to yield 2.4 g (77%) of [[8-acetyl-7-[2-(2-bromoethoxy)ethoxy]-2-naphthalenyl]oxy]acetic acid methyl ester as an oil.

EXAMPLE 7

Preparation of
[[8-acetyl-7-[2-[2-(4-acetyl-3-hydroxy-2-propylphenoxy)ethoxy]ethoxy]-2-naphthalenyl]oxy]acetic acid methyl ester A mixture of 2.4 g of [[8-acetyl-7-[2-[2-bromoethoxy)ethoxy]-2-naphthalenyl]oxy]acetic acid methyl ester, 1.32 g of 1-(2,4-dihydroxy-3-propylphenyl)-ethanone and 1.17 g of anhydrous potassium carbonate in 48 ml of anhydrous acetone and 16 ml of anhydrous dimethylformamide was stirred at reflux for 18 hours. The mixture was filtered and filtrate was concentrated to an oil. The oil was purified by flash column chromatography (10% ethyl acetate-toluene) to yield 2.3 g, mp. 89°–90° C. (76%) of [[8-acetyl-7-[2-[2-(4-acetyl-3-hydroxy-2-propylphenoxy)ethoxy]ethoxy]-2-naphthalenyl]oxy]acetic acid methyl ester.

EXAMPLE 8

Preparation of
[[8-acetyl-7-[2-[2-(4-acetyl-3-hydroxy-2-propylphenoxy)ethoxy]ethoxy]-2-naphthalenyl]oxy]acetic acid A suspension of 2.3 g of [[8-acetyl-7-[2-[2-(4-acetyl-3-hydroxy-2-propylphenoxy)ethoxy]ethoxy]-2-naphthalenyl]oxy]acetic acid methyl ester and 43 ml of 1N sodium hydroxide in 86 ml of methanol was stirred at reflux for 1 hour. The methanol was removed and aqueous solution was acidified to pH 3. The precipitate was extracted with methylene chloride, washed with water, dried (magnesium sulfate) and concentrated in vacuo to give an oil. The oil was triturated with ether to yield 1.9 g, mp 121°–122° C. (84%) of [[8-acetyl-7-[2-[2-(4-acetyl-3-hydroxy-2-propylphenoxy)ethoxy]ethoxy]-2-naphthalenyl]oxy]acetic acid.

EXAMPLE 9

Preparation of
[[8-acetyl-7-[2-[2-(2-bromoethoxy)ethoxy]ethoxy]-2-naphthalenyl]oxy]acetic acid methyl ester Under an argon atmosphere, 2 g of [(8-acetyl-7-hydroxy-2 -naphthalenyl)oxy]acetic acid methyl ester was added to a suspension of 0.38 g of 60% sodium hydride in 30 ml of anhydrous dimethylformamide. The mixture was stirred at room temperature for 40 minutes and then 10 g of bis-(2-bromoethoxy)ethane was added and the mixture was stirred at room temperature for 4 hours. The solvent was removed in vacuo and the residue was dissolved in ethyl acetate, washed with water, dried (magnesium sulfate) and concentrated to give an oil which was purified by high pressure liquid chromatography (45% ethyl acetate-hexane) to yield 2 g (58%) of [[8-acetyl-7-[2-[2-(2-bromoethoxy)ethoxy]ethoxy]-2-naphthalenyl]oxy]acetic acid methyl ester as an oil.

EXAMPLE 10

Preparation of
[[8-acetyl-7-[2-[2-[2-(4-acetyl-3-hydroxy-2-propylphenoxy)ethoxy]ethoxy]ethoxy]-2-naphthalenyl]oxy]acetic acid methyl ester A mixture of 2 g of [[8-acetyl-7-[2-[2-(2-bromoethoxy)ethoxy]ethoxy]-2-naphthalenyl]oxy]acetic acid methyl ester, 1.0 g of 1-(2,4-dihydroxy-3-propylphenyl)ethanone and 0.9 g of anhydrous potassium carbonate in 40 ml of anhydrous acetone and 14 ml of anhydrous dimethylformamide was stirred at reflux for 16 hours. The solvent was removed in vacuo and residue was dissolved in ethyl acetate, washed with water, dried (magnesium sulfate) and concentrated in vacuo to give an oil which was purified by high pressure liquid chromatography (60% ethyl acetate-hexane) to yield 1.8 g (73%) of [[8-acetyl-7-[2-[2-[2-(4-acetyl-3-hydroxy-2-propylphenoxy)ethoxy]ethoxy]ethoxy]-2-naphthalenyl]oxy]acetic acid methyl ester as an oil.

EXAMPLE 11

Preparation of
[[8-acetyl-7-[2-[2-[2-(4-acetyl-3-hydroxy-2-propylphenoxy)ethoxy]ethoxy]ethoxy]-2-naphthalenyl]oxy]acetic acid A solution of 1.8 g of [[8-acetyl-7-[2-[2-[2-(4-acetyl-3-hydroxy-2-propylphenoxy)ethoxy]ethoxy]ethoxy]-2-naphthalenyl]oxy]acetic acid methyl ester and 31 ml of 1N sodium hydroxide in 60 ml of methanol was stirred at reflux for 1 hour. The methanol was removed in vacuo and the aqeuous solution was acidified to pH 3. The gummy precipitate was extracted with methylene chloride, washed with water, dried (magnesium sulfate) and concentrated in vacuo to give an oil which was triturated with ether to yield 1.56 g, m.p. 110°–111° C. (89%) of [[8-acetyl-7-[2-[2-[2-(4-acetyl-3-hydroxy-2-propylphenoxy)ethoxy]ethoxy]ethoxy]-2-naphthalenyl]oxy]acetic acid.

EXAMPLE 12

Preparation of
[[8-acetyl-7-[2-[2-[2-(2-bromoethoxy)ethoxy]ethoxy]-thoxy]-2-naphthalenyl]oxy]acetic acid methyl ester Under an argon atmosphere, 2 g of [(8-acetyl-7-hydroxy-2-naphthalenyl)oxy]acetic acid methyl ester was added to a suspension of 0.32 g of 60% sodium hydride in 30 ml of anhydrous dimethylformamide. The mixture was stirred at room temperature for 40 minutes and then 11.6 g of bis[2-[2-bromoethoxy] ether was added and the mixture was stirred at room temperature for 20 hours. The resulting dark mixture was concentrated in vacuo to an oil which was dissolved in methylene chloride, washed with water and concentrated to give an oil. Purification by high pressure liquid chromatography (35% ethyl acetate-toluene) gave 3.0 g (80%) of [[8-acetyl-7-[2-[2-[2-(2-bromoethoxy)ethoxy]ethoxy]ethoxy]-2-naphthalenyl]oxy]acetic acid methyl ester as an oil.

EXAMPLE 13

Preparation of
[[8-acetyl-7-[2-[2-[2-(2-(4-acetyl-3-hydroxy-2-propylphenoxy)ethoxy]ethoxy]ethoxy]-2-naphthalenyl]oxy]acetic acid methyl ester A mixture of 3 g of [[8-acetyl-7-[2-[2-[2-[2-bromoethoxy]ethoxy]ethoxy]ethoxy]-2-naphthalenyl]oxy]acetic acid methyl ester, 1.36 g of 1-(2,4-dihydroxy-3-propylphenyl) ethanone and 1.2 g of anhydrous potassium carbonate in 60 ml of anhydrous acetone and 20 ml of anhydrous dimethylformamide was stirred at reflux for 18 hours. The mixture was filtered and filtrate was concentrated in vacuo to an oil which was purified by high pressure liquid chromatography (35% ethyl acetate-toluene) to yield 3 g (82%) of [[8-acetyl-7-[2-[2-[2-[2-(4-acetyl-3-hydroxy-2-propylphenoxy)ethoxy]ethoxy]ethoxy]ethoxy]-2-naphthalenyl]oxy]acetic acid methyl ester as an oil.

EXAMPLE 14

Preparation of
[[8-acetyl-7-[2-[2-[2-[2-(4-acetyl-3-hydroxy-2-propylphenoxy]ethoxy]ethoxy]ethoxy]-2-naphthalenyl]oxy]acetic acid A mixture of 3 g of [[8-acetyl-7-[2-[2-[2-[2-(4-acetyl-3-hydroxy-2-propylphenoxy)ethoxy]ethoxy]ethoxy]-thoxy]-2-naphthalenyl]oxy]acetic acid methyl ester and 48 ml of 1N sodium hydroxide in 96 ml of methanol was stirred at reflux for 1 hour. The methanol was removed in vacuo, the aqueous solution was acidified to pH 3 and extracted with methylene chloride. The extract was concentrated to yield an oil which was purified by flash column chromatography (10% methanol-methylene chloride) to give 2.55 g of an oil which was crystallized from ether-ethyl acetate-hexane to yield 1.93 g, m.p. 57°–58° C., (66%) of [[8-acetyl-7-[2-[2-[2-[2-(4-acetyl-3-hydroxy-2-propylphenoxy]ethoxy]ethoxy]ethoxy]-thoxy]-2-naphthalenyl]oxy]acetic acid.

EXAMPLE 15

Preparation of
4-[(7-hydroxy-2-naphthalenyl)oxy]butanoic acid methyl ester

A mixture of 32 g of 2,7-dihydroxynaphthalene and 36 g of potassium carbonate in 250 ml of anhydrous acetone was stirred at room temperature for 1 hour. Ethyl 4-bromobutyrate (31.5 ml) was added and stirring was continued at reflux for 29 hours. The reaction mixture was filtered and the solid was washed well with acetone. The filtrate was concentrated in vacuo and the residue was acidified and extracted with methylene chloride. The extract was washed with two 500 ml portions of 0.5N sodium hydroxide. The combined aqueous layer was left at room temperature for 16 hours and then acidified and extracted with ethyl acetate. The ethyl acetate extract was washed with saturated sodium bicarbonate solution. The sodium bicarbonate layer was acidified and extracted with ethyl acetate and the dried (magnesium sulfate) extract was concentrated in vacuo to a dark solid. This was esterified by refluxing in 300 ml of methanol and 4 ml of concentrated sulfuric acid for 6 hours. The methanol was removed in vacuo and the solid residue was recrystallized from methylene chloride-hexane to give 11.70 g (23% yield), mp 122°–125°, of 4-[(7-hydroxy-2-naphthalenyl)oxy]butanoic acid methyl ester.

EXAMPLE 16

Preparation of
4-[(8-acetyl-7-hydroxy-2-naphthalenyl)oxy]butanoic acid methyl ester Under argon, 2.8 ml of acetyl chloride was added to a suspension of 5.15 g of aluminum chloride in 120 ml of dichloroethane and then 8 g of 4-[(7-hydroxy-2-naphthalenyl)oxy] butanoic acid methyl ester was added. The resulting mixture was stirred at room temperature for 30 minutes and at reflux for 16 hours. The solution was filtered and the dark residue was broken up with 3N hydrochloric acid and extracted with methylene chloride. The filtrate was combined with the methylene chloride extract, washed and dried to give a black oil which was purified by high pressure liquid chromatography, eluting with 2% ethyl acetate/toluene to yield 2.72 g, (29%) of 4-[(8-acetyl-7-hydroxy-2-naphthalenyl)oxy] butanoic acid methyl ester as an oil.

EXAMPLE 17

Preparation of [(4-hydroxy-2-naphthalenyl)oxy]acetic acid methyl ester

A mixture of 1.5180 g of 1,3-dihydroxynaphthalene and 1.70 g of anhydrous potassium carbonate in 10 ml of anhydrous acetone was stirred at room temperature for 1 hour. Methyl bromoacetate (0.91 ml) was added and stirring at room temperature was continued for 50 hours. The solvent was removed in vacuo and the residue was acidified and extracted with ethyl acetate. The dried (magnesium sulfate) extract was concentrated in vacuo and the product was purified by high pressure liquid chromatography using 20% ethyl acetate-toluene to give 0.419 g (19% yield) of [(4-hydroxy-2-naphthalenyl)oxy]acetic acid methyl ester as an oil.

EXAMPLE 18

Preparation of [(4-hydroxy-1-naphthalenyl)oxy]acetic acid methyl ester

A mixture of 16.0 g of 1,4-dihydroxynaphthalene and 18 g of anhydrous potassium carbonate in 100 ml of anhydrous acetone was stirred at room temperature for 2 hours. Methyl bromoacetate (10.5 ml) was added and the reaction mixture was stirred at room temperature for 18 hours and then at reflux for 3 hours. The solvent was removed in vacuo, water and dilute hydrochloric acid were added to the residue and the products were extracted with ethyl acetate. The extract was washed with 1N sodium hydroxide (3×100 ml). The combined aqueous extract was left at room temperature for 3 days and then acidified and extracted with ethyl acetate. The extract was washed with saturated sodium hydrogen carbonate solution and the aqueous layer was acidified. Extraction with ethyl acetate and concentration in vacuo of the dried (magnesium sulfate) extract gave 10.7 g of dark solid. This was esterified by refluxing in 150 ml of methanol with 1.8 ml of concentrated sulfuric acid for 5 hours. The solvent was removed in vacuo and the residue was taken up in ethyl acetate and washed with sodium hydrogen carbonate solution. After concentration in vacuo, the residue was purified by chromatography on 250 g of silica gel. Elution with 5% ethyl acetate-toluene gave 2.7 g of brown solid which was further purified by passing an ether solution through a column of 200 g of acidic alumina (activity III). Concentration of the ether eluent gave 2.5 g (11% yield), mp 127°–131°, of [(4-hydroxy-1-naphthalenyl)oxy]acetic acid methyl ester.

EXAMPLE 19

Preparation of
[(3-acetyl-4-hydroxy-1-naphthalenyl)oxy]acetic acid methyl ester

A mixture of 0.36 g of 2-acetylnaphthalene-1,4-diol and 0.35 g of anhydrous potassium carbonate in 10 ml of anhydrous acetone was stirred at room temperature for 1 hour. Methyl bromoacetate (0.17 ml) was added and stirring was continued for 66 hours. The solvent was removed in vacuo, and the residue was acidified and extracted with ethyl acetate. The dried(magnesium sulfate)extract was concentrated in vacuo and the solid residue was recrystallized from methanol-methylene chloride to give 0.14 g (29% yield), mp 123°–124°, of [(3-acetyl-4-hydroxy-1-naphthalenyl)oxy]acetic acid methyl ester.

EXAMPLE 20

Preparation of [(5-hydroxy-1-naphthalenyl)oxy]acetic acid methyl ester

A mixture of 16 g (0.1 mole) of 1,5-dihydroxynaphthalene and 18 g (0.13 mole) of anhydrous potassium carbonate in 100 ml of anhydrous acetone was stirred at room temperature for 3 hours. Methyl bromoacetate (10.5 ml, 0.11 mole) was added and stirring at room temperature was continued for 18 hours and then at reflux for 3 hours. The solvent was removed in vacuo, the residue was acidified and the product was extracted with ethyl acetate. The extract was washed with 1N sodium hydroxide (3×100 ml) and the aqueous layer was left at room temperature for 16 hours. The solution was acidified and extracted with ethyl acetate. The extract was washed with saturated sodium bicarbonate solution and the aqueous layer was acidified and extracted with ethyl acetate. The dried (magnesium sulfate) extract was concentrated in vacuo to a solid which was esterified by refluxing 3 hours in 100 ml of methanol and 1.5 ml of concentrated sulfuric acid. The solvent was removed in vacuo and the residue was taken up in methylene chloride and washed with 5% sodium bicarbonate solution. The dried (magnesium sulfate) extract was concentrated in vacuo to a dark solid which was chromatographed on 100 g of silica gel. Elution with 25% ethyl acetate-hexane and recrystallization of the pure fractions from methylene chloride-hexane gave 2.3 g (10% yield), mp 177°–179°, of [(5-hydroxy-1-naphthalenyl)oxy]acetic acid methyl ester.

EXAMPLE 21

Preparation of
[(6-acetyl-5-hydroxy-1-naphthalenyl)oxy]acetic acid methyl ester

To a suspension of 0.887 mg of [(5-hydroxy-1-naphthalenyl)oxy]acetic acid methyl ester in 20 ml of anhydrous nitromethane cooled in an ice bath was added 0.52 ml of stannic chloride. This dark solution was stirred 5 minutes and then 0.33 ml of acetyl chloride was added. The cooling bath was allowed to warm slowly to 15° while stirring of the reaction mixture was continued for 2.5 hours. Ice and 6N hydrochloric acid were added and the product was extracted with ethyl acetate. The extract was washed with sodium bicarbonate solution, dried (magnesium sulfate) and concentrated in vacuo. The residue was chromatographed on 100 g of silica gel. Elution with 5% ethyl acetate-toluene gave 0.423 g (41% yield), mp 130°–135°, of [(6-acetyl-5-hydroxy-1-naphthalenyl)oxy]acetic acid methyl ester.

EXAMPLE 22

Preparation of
1-(1,6-dihydroxy-2-naphthalenyl)ethanone

To a solution of 8.3 g of aluminum chloride and 3.6 ml of acetyl chloride in 60 ml of anhydrous nitromethane at room temperature was added 8.0 g of 1,6dihydroxynaphthalene. The reaction mixture was stirred under argon at 23° for 20 hours and then concentrated in vacuo. The residue was treated with 6N hydrochloric acid and extracted with ethyl acetate. The extract was washed with sodium bicarbonate solution, dried (magnesium sulfate) and concentrated in vacuo. The crude product was chromatographed on 250 g of silica gel. Elution with 2% ethyl acetatetoluene gave 3.6 g (36% yield), mp 195°–200°, of 1-(1,6-dihydroxy-2-naphthalenyl)ethanone.

EXAMPLE 23

Preparation of
[(6-acetyl-5-hydroxy-2-naphthalenyl)oxy]acetic acid methyl ester

A mixture of 2.81 g of 1-(1,6-dihydroxy-2-naphthalenyl)ethanone and 2.90 g of potassium carbonate in 75 ml of anhydrous acetone was stirred at 23° for 1 hour. Methyl bromoacetate (1.5 ml) was added and the reaction mixture was stirred at 23° for 18 hours. The solid was removed by filtration and the filtrate was concentrated in vacuo. The residue was treated with 1N hydrochloric acid and extracted with ethyl acetate. The dried (magnesium sulfate) extract was concentrated in vacuo and the crude solid was purified by recrystallization from ethyl acetate-hexane to give 2.30 g (61% yield), mp 118°–120°, of [(6-acetyl-5-hydroxy-2-naphthalenyl)oxy]acetic acid methyl ester.

EXAMPLE 24

Preparation of
1-(1,7-dihydroxy-2-naphthalenyl)ethanone

To 6.75 g of aluminum chloride in 50 ml of anhydrous nitromethane was added 2.9 ml of acetyl chloride. To the stirred solution at room temperature was added 6.40 g of 1,7-dihydroxynaphthalene and the mixture was stirred at room temperature for 16 hours. The solvent was removed in vacuo and the residue was treated with 6N hydrochloric acid and extracted with methylene chloride. The dried (magnesium sulfate) extract was chromatographed on 330 g of silica gel. Elution with 20% ethyl acetate-toluene gave 6.0 g of orange solid which was recrystallized from methylene chloride-ether-hexane to give 2.60 g, mp 214°–217°, of 1-(1,7-dihydroxy-2-naphthalenyl)ethanone. A second crop of 1.50 g of pure material was obtained on further concentration making the total yield 51%.

EXAMPLE 25

Preparation of
[(7-acetyl-8-hydroxy-2-naphthalenyl)oxy]acetic acid methyl ester

A mixture of 3.577 g of 1-(1,7-dihydroxy-2-naphthalenyl)ethanone and 3.70 g of anhydrous potassium carbonate in 100 ml of anhydrous acetone was stirred at room temperature for 50 minutes. Methyl bromoacetate (1.7 ml) was added and stirring was continued for 18 hours. The reaction mixture was filtered and the filtrate was concentrated in vacuo to a residue which was acidified and extracted with ethyl acetate. The dried (magnesium sulfate) extract was concentrated in vacuo and the solid residue was recrystallized from methylene chloride-ether to give 1.87 g, mp 133°–135°, of [(7-acetyl-8-hydroxy-2-naphthalenyl)oxy]acetic acid methyl ester. A second crop of 0.38 g was obtained making the total yield 46%.

EXAMPLE 26

Preparation of 7-(2-propenyloxy)-2-naphthalenol

A mixture of 36 g of 2,7-dihydroxynaphthalene and 40 g of anhydrous potassium carbonate in 250 ml of anhydrous acetone was stirred vigorously at room temperature for 2.5 hours. Allyl bromide (21.9 ml) was added and the mixture was stirred at 23° for 19 hours. The reaction mixture was filtered and the solid was washed well with acetone. The filtrate was concentrated in vacuo and the residue was acidified and extracted with methylene chloride. The extract was washed with three 200 ml of portions of 1N sodium hydroxide. The combined aqueous layer was acidified and extracted with methylene chloride. The dried (magnesium sulfate) extract was concentrated in vacuo and the residue was purified by chromatography on 250 g of silica gel. Elution with 10% ethyl acetate-toluene gave 17.7 g of somewhat impure product. Crystallization from etherhexane gave 7.9 g, mp 78°–80°, of 7-(2-propenyloxy)-2-naphthalenol.

EXAMPLE 27

Preparation of
[(7-(2-propenyloxy)-2-naphthalenyl]oxy]acetic acid methyl ester

A mixture of 7.9 g of 7-(2-propenyloxy)-2-naphthalenol and 8.3 g of potassium carbonate in 50 ml of anhydrous acetone was stirred at room temperature for 1.5 hours. Methyl bromoacetate (4.7 ml) was added and stirring was continued for 18 hours. The reaction mixture was filtered and the filtrate was concentrated in vacuo to yield (8.4 g) of [[7-(2-propenyloxy)-2-naphthalenyl]oxy]acetic acid methyl ester, mp 69°–70° after recrystallization from ether-hexane.

EXAMPLE 28

Preparation of
[[7-hydroxy-8-(2-propenyl)-2-naphthalenyl]oxy]acetic acid methyl ester 8.414 g of [[7-(2-propenyloxy)-2-naphthalenyl]oxy]acetic acid methyl ester was heated in an oil bath at 190° for 2 hours and 15 minutes. The solid obtained on cooling was recrystallized from methylene chloride-hexane to give 6.41 g (76% yield), mp 128°–130°, of [[7-hydroxy-8-(2-propenyl)-2-naphthalenyl]oxy]acetic acid methyl ester.

EXAMPLE 29

Preparation of
[(7-hydroxy-8-propyl-2-naphthalenyl)oxy]acetic acid methyl ester

A solution of 6.415 g of [[7-hydroxy-8-(2-propenyl)-2-naphthalenyl]oxy]acetic acid methyl ester in 100 ml of ethyl acetate and 0.7 g of 10% palladium on carbon was shaken in a Parr hydrogenator at room temperature and an initial pressure of 52 psi for 1 hour. The reaction mixture was filtered through Celite and the filtrate was concentrated in vacuo to give 6.25 g (97% yield), mp 122°–124°, of [(7-hydroxy-8-propyl-2-naphthalenyl)oxy]acetic acid methyl ester.

EXAMPLE 30

Preparation of
4-[[8-acetyl-7-[2-(2-bromoethoxy)ethoxy]-2-naphthalenyl]oxy]butanoic acid methyl ester Under an argon atmosphere, 2 g (0.007 mol) of 4-[(8-acetyl-7-hydroxy-2-naphthalenyl)oxy]-butanoic acid methyl ester in 5 ml of anhydrous dimethylformamide was added to a suspension of 0.29 g of sodium hydride in 25 ml of anhydrous dimethylformamide. The mixture was stirred at room temperature for 20 minutes and then 7.7 g of bis-(2-bromoethyl)ether was added and the mixture was stirred at room temperature for 20 hours. The solvent was removed and residual oil was purified by high pressure liquid chromatography using 25% ethyl acetate-hexane to yield 1.6 g (54%) of 4-[[8-acetyl-7-[2-(2-bromoethoxy)ethoxy]-2-naphthalenyl]oxy]-butanoic acid methyl ester as an oil.

EXAMPLE 31

Preparation of
4-[[8-acetyl-7-[2-[2-(4-acetyl-3-hydroxy-2-propylphenoxy)ethoxy]ethoxy]-2-naphthalenyl)oxy]butanoic acid methyl ester A mixture of 1.6 g of 4-[[8-acetyl-7-[2-(2-bromoethoxy)ethoxy]-2-naphthalenyl]oxy]butanoic acid methyl ester, 0.82 g of 1-(2,4-dihydroxy-3-propylphenyl)-ethanone and 0.73 g of anhydrous potassium carbonate in 33 ml of anhydrous acetone and 11 ml of anhydrous dimethylformamide was stirred at reflux for 16 hours. The mixture was filtered and filtrate was concentrated to an oil. The oil was purified by high pressure liquid chromatography using 50% ethyl acetate-hexane to give 1.72 g (86%) of 4-[[8-acetyl-7-[2-[2-(4-acetyl-3-hydroxy-2-propylphenoxy)ethoxy]ethoxy]-2-naphthalenyl)oxy]butanoic acid methyl ester as an oil.

EXAMPLE 32

Preparation of 4-[[8-acetyl-7-[2-[2-(4-acetyl-3-hydroxy-2-propylphenoxy)ethoxy]ethoxy]-2-naphthalenyl]oxy]butanoic acid A solution of 1.7 g of 4-[[8-acetyl-7-[2-[2-(4-acetyl-3-hydroxy-2-propylphenoxy)ethoxy]ethoxy]-2-naphthalenyl]oxy]butanoic acid methyl ester and 30 ml of 1N sodium hydroxide in 60 ml of methanol was stirred at reflux for 1 hour. The methanol was removed in vacuo and the aqueous solution was acidified to pH 3. The gummy precipitate was extracted with methylene chloride, the extract was washed with water, dried (magnesium sulfate) and concentrated in vacuo to an oil. The oil was triturated with hexane-ether to yield 1.4 g, m.p. 71°–75° C. (85%) of 4-[[8-acetyl-7-[2-[2-(4-acetyl-3-hydroxy-2-propylphenoxy)ethoxy]ethoxy]-2-naphthalenyl]oxy]butanoic acid.

EXAMPLE 33

When [7-hydroxy-2-naphthalenyl)oxy]acetic acid methyl ester is reacted with bis-(3-bromopropyl)ether in accordance with Example 3 and the product is then reacted with 1-(2,4-dihydroxy-3-propylphenyl)ethanone, in accordance with Example 4, an ester is obtained which can be hydrolyzed to give [[7-[3-[3-(4-acetyl-3-hydroxy-2-propylphenoxy)propoxy]propoxy]-2-naphthalenyl]oxy]acetic acid.

EXAMPLE 34

When 4-[(7-hydroxy-2-naphthalenyl)oxy]butanoic acid ethyl ester is reacted with bis-(3-bromopropyl)ether in accordance with Example 3 and the product is then reacted with 1-(2,4-dihydroxy-3-propylphenyl)ethanone in accordance with Example 4, an ester is obtained which can be hydrolyzed to give 4-[[7-[3-[3-(4-acetyl-3-hydroxy-2-propylphenoxy)propoxy]propoxy]-2-naphthalenyl]oxy]butanoic acid.

EXAMPLE 35

When [(4-hydroxy-2-naphthalenyl)oxy]acetic acid methyl ester is reacted with bis-(3-bromopropyl)ether in accordance with Example 3 and the product is then reacted with 1-(2,4-dihydroxy-3-propylphenyl)ethanone in accordance with Example 4, an ester is obtained which can be hydrolyzed to give [[4-[3-[3-(4-acetyl-3-hydroxy-2-propylphenoxy)propoxy]propoxy]-2-naphthalenyl]oxy]acetic acid.

EXAMPLE 36

When [(4-hydroxy-1-naphthalenyl)oxy]acetic acid methyl ester is reacted with bis-(3-bromopropyl)ether in accordance with Example 3 and the product is then reacted with 1-(2,4-dihydroxy-3-propylphenyl)ethanone in accordance with Example 4, an ester is obtained which can be hydrolyzed to give [[4-[3-[3-(4-acetyl-3-hydroxy-2-propylphenoxy)propoxy]propoxy]-1-naphthalenyl]oxy]acetic acid.

EXAMPLE 37

When [(5-hydroxy-1-naphthalenyl)oxy]acetic acid methyl ester is reacted with bis-(3-bromopropyl)ether in accordance with Example 3 and the product is then reacted with 1-(2,4-dihydroxy-3-propylphenyl)ethanone in accordance with Example 4, an ester is obtained which can be hydrolyzed to give [[5-[3-[3-(4-acetyl-3-hydroxy-2-propylphenoxy)propoxy]propoxy]-1-naphthalenyl]oxy]acetic acid.

EXAMPLE 38

When [(3-acetyl-4-hydroxy-1-naphthalenyl)oxy]acetic acid methyl ester is reacted with bis-(3-bromopropyl)ether in accordance with Example 3 and the product, which [[3-acetyl-4-[3-(3-bromopropoxy)propoxy]-1-naphthalenyl]oxy]acetic acid methyl ester, is then reacted with 1-(2,4-dihydroxy-3-propylphenyl)ethanone in accordance with Example 4, an ester is obtained which can be hydrolyzed to give [[3-acetyl-4-[3-[3-(4-acetyl-3-hydroxy-2-propylphenoxy)propoxy]propoxy]-1-naphthalenyl]oxy]acetic acid.

EXAMPLE 39

When [(6-acetyl-5-hydroxy-2-naphthalenyl)oxy]acetic acid methyl ester is reacted with bis-(3-bromopropyl)ether in accordance with Example 3 and the product is then reacted with 1-(2,4-dihydroxy-3-propylphenyl)ethanone in accordance with Example 4, an ester is obtained which can be hydrolyzed to give [[6-acetyl-5-[3-[3-(4-acetyl-3-hydroxy-2-propylphenoxy)propoxy]propoxy]-2-naphthalenyl]oxy]acetic acid.

EXAMPLE 40

When [(7-acetyl-8-hydroxy-2-naphthalenyl)oxy]acetic acid methyl ester is reacted with bis[2-(2-bromoethoxy)ethyl]ether in accordance with Example 12 and the product is then reacted with 1-(2,4-dihydroxy-3-propylphenyl)ethanone in accordance with Example 13, an ester is obtained which can be hydrolyzed to give [[7-acetyl-8-[2-[2-[2-[2-(4-acetyl-3-hydroxy-2-propylphenoxy)ethoxy]ethoxy]ethoxy]ethoxy]-2-naphthalenyl]oxy]acetic acid.

EXAMPLE 41

When [(6-acetyl-5-hydroxy-1-naphthalenyl)oxy]acetic acid methyl ester is reacted with bis-(3-bromopropyl)ether in accordance with Example 3 and the product is then reacted with 1-(2,4-dihydroxy-3-propylphenyl)ethanone in accordance with Example 4, an ester is obtained which can be hydrolyzed to give [[6-acetyl-5-[3-[3-(4-acetyl-3-hydroxy-2-propylphenoxy)propoxy]propoxy]-1-naphthalenyl]oxy]acetic acid.

EXAMPLE 42

| | CAPSULE FORMULATION | | | |
| --- | --- | --- | --- | --- |
| | mg/capsule | | | |
| Ingredients | 25 mg | 50 mg | 100 mg | 200 mg |
| [[8-acetyl-7-[3-[3-(4-acetyl-3-hydroxy-2-propylphenoxy)propoxy]propoxy]-2-naphthalenyl]oxy] acetic acid | 25 | 50 | 100 | 200 |
| Lactose | 375 | 155 | 200 | 140 |
| Starch | 30 | 30 | 35 | 40 |
| Talc | 20 | 15 | 15 | 20 |
| Weight of capsule | 450 mg | 250 mg | 350 mg | 400 mg |

Procedure:

Mix [[8-acetyl-7-[3-[3-(4-acetyl-3-hydroxy-2-propylphenoxy)propoxy]propoxy]-2-naphthalenyl]oxy]acetic acid, lactose and starch in a suitable mixer. Mill. Add talc and mix well. Encapsulate on suitable equipment.

EXAMPLE 43

TABLET FORMULATION
(Wet granulation)

| Ingredients | mg/tablet | | | |
|---|---|---|---|---|
| | 25 mg | 50 mg | 100 mg | 200 mg |
| [[8-acetyl-7-[3-[3-(4-acetyl-3-hydroxy-2-propyl-phenoxy)propoxy]propoxy]-2-naphthalenyl]oxy] acetic acid. | 25 | 50 | 100 | 200 |
| Lactose | 280 | 153 | 187 | 171 |
| Modified Starch | 55 | 25 | 35 | 45 |
| Pregelatinized Starch | 35 | 20 | 25 | 30 |
| Distilled water q.s. | | | | |
| Magnesium Stearate | 5 | 2 | 3 | 4 |
| Weight of tablet | 400 mg | 250 mg | 350 mg | 450 mg |

Procedure:

Mix, [[8-acetyl-7-[3-[3-(4-acetyl-3-hydroxy-2-propylphenoxypropoxy]propoxy]-2-naphthalenyl]oxy]acetic acid, lactose, modified starch and pregelatinized starch in a suitable mixer. Granulate with sufficient distilled water to proper consistency. Mill. Dry in a suitable oven. Mill and mix with magnesium stearate for 3 minutes. Compress on a suitable press equipped with appropriate punches.

EXAMPLE 44

TABLET FORMULATION
(Direct Compression)

| Ingredients | mg/tablet 25 mg |
|---|---|
| [[8-acetyl-7-[3-[3-(4-acetyl-3-hydroxy-2-propylphenoxy)propoxy]propoxy]-2-naphthalenyl]oxy acetic acid. | 25 |
| Lactose | 181 |
| Avicel | 55 |
| Direct Compression Starch | 35 |
| Magnesium Stearate | 4 |
| Weight of tablet | 300 mg |

Procedure:

Mix [[8-acetyl-7-[3-[3-(4-acetyl-3-hydroxy-2-propylphenoxy)propoxy]propoxy]-2-naphthalenyl]oxy]acetic acid with an equal amount of lactose. Mix well. Mix with avicel and direct compression starch, and the remaining amount of lactose. Mix well. Add magnesium stearate and mix for 3 minutes. Compression on a suitable press equipped with appropriate punches.

I claim:

1. A compound of the formula

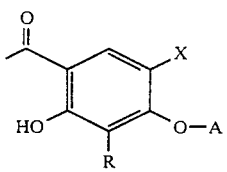

I wherein R is hydrogen or lower alkyl, X is hydrogen or halogen, and A is the group

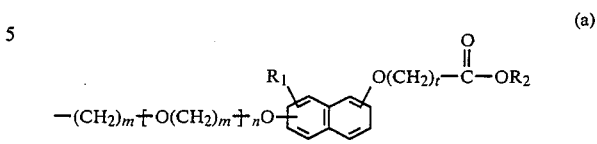

(a)

, or

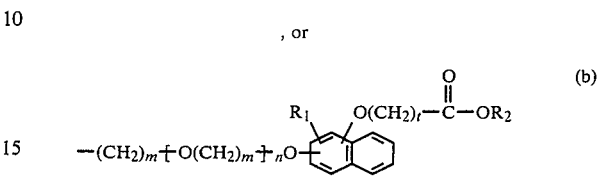

(b)

wherein $R_1$ is hydrogen, acyl or lower alkyl, $R_2$ is hydrogen or lower alkyl, m is an integer from 2 to 4, n is an integer from 1 to 3, and t is an integer from 1 to 5, provided that $R_1$ is adjacent to $-(CH_2)_{\overline{m}}[O(CH_2)_{m^-}]_{\overline{n}}O-$, and, when $R_2$ is hydrogen, a salt thereof with a pharmaceutically acceptable base.

2. A compound, in accordance with claim 1, wherein A is

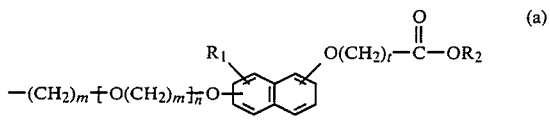

(a)

wherein X is hydrogen, R is lower alkyl, $R_1$ is alkanoyl, and $R_2$ is hydrogen.

3. A compound, in accordance with claim 1, wherein A is

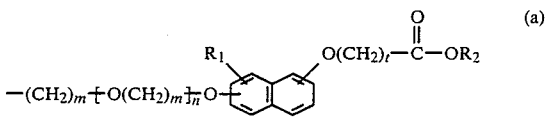

(a)

wherein X is hydrogen, R is propyl, $R_1$ is acetyl, $R_2$ is hydrogen, m is 2 or 3, and t is 1 or 3.

4. A compound, in accordance with claim 1, wherein A is

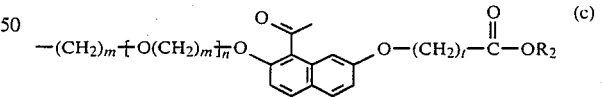

(c)

wherein X is hydrogen, R is propyl, $R_2$ is hydrogen, m is 2 or 3, and t is 1 or 3.

5. The compound, in accordance with claim 1, [[8-acetyl-7-[3-[3-(4-acetyl-3-hydroxy-2-propylphenoxy)propoxy]propoxy]-2-naphthalenyl]oxy]acetic acid.

6. The compound, in accordance with claim 1, [[8-acetyl-7-[2-[2-(4-acetyl-3-hydroxy-2-propylphenoxy)ethoxy]ethoxy]-2-naphthalenyl]oxy]acetic acid.

7. The compound, in accordance with claim 1, [[8-acetyl-7-[2-[2-[2-(4-acetyl-3-hydroxy-2-propylphenoxy)ethoxy]ethoxy]ethoxy]-2-naphthalenyl]oxy]acetic acid.

8. The compound, in accordance with claim 1, [[8-acetyl-7-[2-[2-[2-[2-(4-acetyl-3-hydroxy-2-propylphenoxy]ethoxy]ethoxy]ethoxy]-2-naphthalenyl]oxy]acetic acid.

9. The compound, in accordance with claim 1, 4-[[8-acetyl-7-[2-[2-(4-acetyl-3-hydroxy-2-propylphenoxy)ethoxy]ethoxy]-2-naphthalenyl]oxy]butanoic acid.

10. A method of treating allergies which comprises administering to a host requiring such treatment an effective amount of a compound of the formula

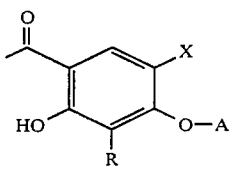
I wherein R is hydrogen or lower alkyl, X is hydrogen or halogen, and A is the group

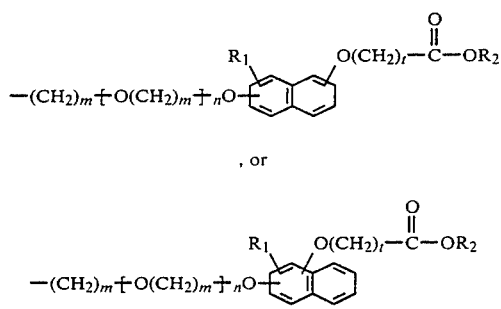

wherein $R_1$ is hydrogen, acyl or lower alkyl, $R_2$ is hydrogen or lower alkyl, m is an integer from 2 to 4, n is an integer from 1 to 3, and t is an integer from 1 to 5, provided that $R_1$ is adjacent to —$(CH_2)_m[O(CH_2)_m\text{-}]_nO$—, and when $R_2$ is hydrogen, a salt thereof with a pharmaceutically acceptable base.

11. A pharmaceutical composition comprising a compound of the formula

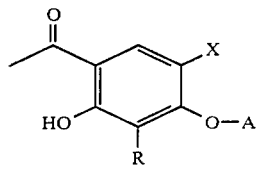
I wherein R is hydrogen or lower alkyl, X is hydrogen or halogen, and A is the grooup

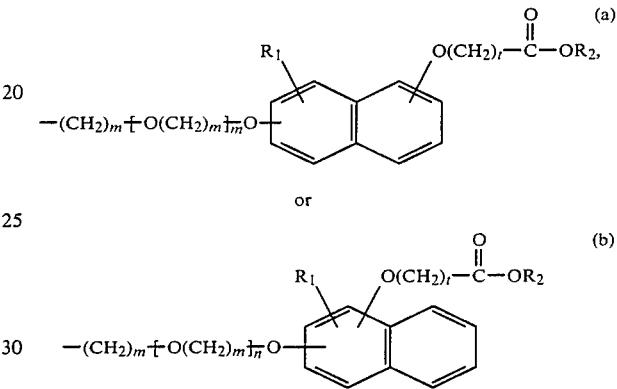

wherein $R_1$ is hydrogen, acyl or lower alkyl, $R_2$ is hydrogen or lower alkyl, m is an integer from 2 to 4, n is an integer from 1 to 3, and t is an integer from 1 to 5, provided that $R_1$ is adjacent to —$(CH_2)_m[O(CH_2)_m\text{-}]_nO$—, and when $R_2$ is hydrogen, a salt thereof with a pharmaceutically acceptable base, and an inert pharmaceutical carrier.

* * * * *